United States Patent
Schubert et al.

(10) Patent No.: US 7,745,223 B2
(45) Date of Patent: Jun. 29, 2010

(54) DEVICE WITH NOVEL AND IMPROVED SURFACE PROPERTIES

(75) Inventors: Axel Schubert, Munich (DE); Stefan Wurlitzer, Grasbrunn (DE); Andreas Calatzis, Munich (DE); Martin Glauner, Grenzach-Wyhlen (DE)

(73) Assignee: C A Casyso AG (CH)

( * ) Notice: Subject to any disclaimer, the term of this patent is extended or adjusted under 35 U.S.C. 154(b) by 1116 days.

(21) Appl. No.: 11/200,494

(22) Filed: Aug. 10, 2005

(65) Prior Publication Data

US 2006/0034734 A1 Feb. 16, 2006

Related U.S. Application Data

(60) Provisional application No. 60/600,831, filed on Aug. 12, 2004.

(30) Foreign Application Priority Data

Aug. 12, 2004 (GB) ................... 0418474.3

(51) Int. Cl.
*G01N 33/86* (2006.01)
(52) U.S. Cl. ............... 436/69; 436/63; 436/153; 436/174; 422/73; 422/99; 422/101; 422/102; 73/64.41; 600/369
(58) Field of Classification Search ............. 436/63, 436/69, 149, 153, 174; 422/68.1, 73, 82.01, 422/99, 101, 102; 435/13; 73/64.41, 64.42; 600/369
See application file for complete search history.

(56) References Cited

U.S. PATENT DOCUMENTS

| | | | |
|---|---|---|---|
| 3,714,815 A | 2/1973 | Hartert et al. | |
| 4,148,216 A | 4/1979 | Do et al. | |
| 4,193,293 A | 3/1980 | Cavallari | |
| 4,341,111 A | 7/1982 | Husar | |
| 5,223,227 A | 6/1993 | Zuckerman | |
| 5,246,451 A * | 9/1993 | Trescony et al. | ........... 427/2.25 |
| 5,262,451 A | 11/1993 | Winters et al. | |
| 5,302,348 A * | 4/1994 | Cusack et al. | ................. 422/73 |

(Continued)

FOREIGN PATENT DOCUMENTS

DE   100 03 093 A1   8/2001

(Continued)

OTHER PUBLICATIONS

Hartert, Blutgerinnung mit der Thrombelastographie, einem neuen Untersuchungsverfahren (Coagulation studies with thrombeblastography, a new test method); *Klinische Wochenschrift*, vol. 26, No. 37/38, pp. 577-583 (Oct. 1948).

*Primary Examiner*—Maureen M Wallenhorst
(74) *Attorney, Agent, or Firm*—Joyce v. Natzmer; Pequignot + Myers (57) ABSTRACT

To increase the adhesion strength of coagulated blood on a surface by increasing the surface interaction of blood-inherent components like fibrin/fibrinogen and thrombocytes it is described to treat the surface by exposing it to ionized atoms or molecules. The surface treatment according to the invention is applied on plastic disposables used in blood diagnostics (e.g. hemostasis analysis) as well as medical implants like artery sealings. The improved blood clot adhesion results in higher diagnostic security due to reduced measurement failure (e.g., for patients with increased thrombocyte content) and in better significance of special tests (e.g., hyperfibrinolysis diagnosis).

18 Claims, 7 Drawing Sheets

U.S. PATENT DOCUMENTS

| | | |
|---|---|---|
| 5,344,611 A | 9/1994 | Vogler et al. |
| 5,455,009 A | 10/1995 | Vogler et al. |
| 5,591,140 A | 1/1997 | Narayanan et al. |
| 5,627,079 A | 5/1997 | Gardella, Jr. et al. |
| 5,723,219 A | 3/1998 | Kolluri et al. |
| 5,777,215 A | 7/1998 | Calatzis et al. |
| 6,159,531 A | 12/2000 | Dang et al. |
| 6,417,004 B1 | 7/2002 | Brady et al. |
| 6,537,819 B2 | 3/2003 | Cohen et al. |

FOREIGN PATENT DOCUMENTS

| | | |
|---|---|---|
| EP | 0404456 | 12/1990 |
| EP | 0629445 A2 | 12/1994 |
| EP | 0635720 A2 | 1/1995 |
| EP | 126631 A1 | 12/2002 |
| IE | 70604 | 12/1996 |
| WO | WO 02/066958 A1 | 8/2002 |

* cited by examiner

DEVICE WITH NOVEL AND IMPROVED SURFACE PROPERTIES

This application claims the benefit of U.S. provisional application No. 60/600,831, filed Aug. 12, 2004, which is incorporated herein by reference in its entirety.

TECHNICAL FIELD

The invention relates to the field of medical applications requiring increased adhesion strengths of clotting or clotted blood or a clot of blood components on artificial surfaces, e.g. for blood coagulation diagnosis (hemostasis analysis) or vascular treatment.

BACKGROUND OF THE INVENTION

It is essential for survival that a wound stops bleeding, i.e. that the body possesses an adequate mechanism for hemostasis. The process of blood clotting can be activated in the case of injuries or inflammations by either extrinsic or intrinsic factors, e.g. tissue factor (TF) or Hagemann factor (F XII), respectively. Both activation channels are continued in a common branch of the cascade resulting in thrombin formation. The thrombin itself finally initiates the formation of fibrin fibers, which represent the protein backbone of blood clots.

Various methods have been introduced to assess the potential of blood to form an adequate clot and to determine the blood clots stability. One group of tests is summarized by the term "viscoelastic methods". The common feature of these methods is that the blood clot firmness (or other parameters dependent on it) is continuously determined, from the formation of the first fibrin fibers, till the dissolution of the blood clot by fibrinolysis. Blood clot firmness is a functional parameter, which is important for hemostasis in vivo, as a clot must resist blood pressure and shear stress at the site of vascular injury. Clot firmness results from multiple interlinked processes: coagulation activation, thrombin formation, fibrin formation and polymerisation, platelet activation and fibrin-platelet interaction and can be compromised by fibrinolysis. Thus, by the use of the viscoelastic monitoring all these mechanisms of the coagulation system can be assessed.

The publications and other materials referred to herein to illustrate the invention and, in particular, to provide additional details respecting the practice are incorporated herein by reference.

The first viscoelastic method was called "thrombelastography" (Hartert H: Blutgerinnungsstudien mit der Thrombelastographie, einem neuen Untersuchungsverfahren. Klin Wochenschrift 26:577-583, 1948). In the thromboelastography, the sample is placed in a cup that is periodically rotated to the left and right by about 5°. A pin is freely suspended by a torsion wire. When a clot is formed it starts to transfer the movement of the cup to the pin against the reverse momentum of the torsion wire. The movement of the pin is continuously recorded and plotted against time.

The fibrin backbone creates a mechanical, elastic linkage between the two surfaces of the blood-containing cup and a pin plunged therein. A proceeding coagulation process induced by adding one or more activating factor(s) can thus be observed. In this way, various deficiencies of a patient's hemostatic status can be revealed and used for proper medical intervention.

Modifications of the original thromboelastography technique (also called thromboelastometry) have been described by Cavallari et al. (U.S. Pat. No. 4,193,293), by Do et al. (U.S. Pat. No. 4,148,216), by Cohen (U.S. Pat. No. 6,537,819), by Hartert et al. (U.S. Pat. No. 3,714,815) and by Calatzis et al. (U.S. Pat. No. 5,777,215).

A common feature of all the methods used for coagulation diagnosis is that the blood clot is placed between two cylindrical bodies and the ability of the blood clot to couple those two bodies is determined. However, the measurement can only be evaluated as long as the fibrin network is sufficiently bound to the surfaces of these two bodies, i.e. of cup and pin. If the fibers tear off even partly, the disturbed measurement becomes hard to interpret because of interference between this effect and the pathologic pattern of hyperfibrinolysis. Unfortunately, such tear-offs of the fibrin network can occur in the case of increased thrombocyte concentrations as observable for example in the blood of hematologic patients (thrombocytosis). In these patients the strength of the blood clot is enhanced and this can lead to too strong forces on the plastic surface, which can tear the clot off the material. For that reason, an enhancement of the blood-clot adhesion strength would improve the therapeutic security considerably.

The original cup and pin material used for thromboelastometry during the forties until the seventies was stainless steel. These cups and pins were cleaned between measurements and reused.

When thromboelastometry was developed most devices used in the medical laboratory were reused and were usually made of steel, other metals, glass or other durable materials. During the sixties and seventies most of these devices have been exchanged by disposable items made of plastic. These plastic parts are usually economically produced by injection moulding or equivalent techniques.

Disposable cups and pins for the use in thromboelastometry have been described in U.S. Pat. No. 4,148,216 by Do et al and in U.S. Pat. No. 5,223,227 by Zuckerman. In the U.S. Pat. No. 5,223,227 a production process for the cup and pin material is disclosed, which involves a roughening process of the moulds used for the injection moulding of the cups and pins. Roughening of the mould is the common strategy for enhancing the surface roughness of plastic parts produced by injection moulding. In the U.S. Pat. No. 5,223,227 mechanically roughening of the mould by sand-blasting is described.

The approach of roughening the mould to roughen the surface of the cup and pin to thereby enhance the adhesion of blood on the surface of the cup and the pin has several disadvantages:

The blood-plastic interaction takes place especially in a microscopic range of the single plastic and of the fibrin molecules. In contrast, the roughness produced by the injection moulding process is in a much larger range. Because of this the plastic surfaces produced by injection moulding provide only a limited adhesion of the blood clot. This may be sufficient for the analysis of normal blood, but may be inadequate when factors are present in the blood which compete with the adhesion of fibrin onto the plastic surfaces.

To obtain a reproducible adhesion of blood on a surface it is important to have a reproducible surface roughness.

However, the surface roughness of the injection mould changes during long-term use of the mould and also varies when a new mould has to be produced, or when several cavities are used for the production of the same part (in multi-cavity injection moulding tools).

The process for reaching an identical surface roughness on an injection moulding tool compared to previously applied tools can be very expensive and time-consuming. Several surface modifications may need to be performed, sample parts have to be produced and evaluated.

In addition, the surface properties produced by injection moulding vary depending on several injection moulding parameters (pressure, temperature) as well as by the batch of the plastic material applied.

The need for improved blood-clot anchoring at artificial surfaces also exists for implants or special artery sealings. In both cases the surface properties must allow a sufficient adhesion of coagulated blood. In the case of implants the blood clot serves as a scaffold for tissue regeneration. Although most polymeric surfaces show in general a good ability to bind blood-inherent coagulation components like thrombocytes and fibrin, the maximum tearing force is not adequate in the case of higher blood pressures or vascular motions. In view of this, improvements of the blood anchoring ability at artificial surfaces enable the use of highly sufficient vascular sealings.

In conclusion a method to improve the adhesion strength of blood clots onto plastic surfaces for diagnostic as well as for biomedical uses is highly desirable.

In the last decade, a rather overwhelming number of plasma applications to enhance the biocompatibility of medical devices in blood contact was disclosed (e.g. U.S. Pat. No. 6,159,531; U.S. Pat. No. 5,591,140; U.S. Pat. No. 5,262,451). These attempts were made to reduce the common blood affinity of artificial surfaces, thus preventing disadvantageous blood clotting and/or tissue deposition. The reported applications contain surgical equipments and in-vivo implants as well as disposables for blood storage or diagnostic purposes.

From U.S. Pat. No. 5,344,611 it is known to treat the surface of, e.g. polystyrene parts with plasma, to further accelerate the clotting activation of blood in contact to surfaces made from such polymers.

There remains a need for a device to the surface of which a blood clot adheres with high adhesion strength. There is also a need for a method for preparing a surface such that the adhesion of a blood clot or to a clot of blood components to the surface is enhanced. In addition, there is a need for a device for more reliable coagulation analysis.

The present invention is directed to a method of treating the surface of a device which is to be coupled to a clot of blood or to a clot of blood components, a device which is to be coupled to a clot of blood or to a clot of blood components and a device for coagulation analysis.

The method of treating the surface is especially advantageous in that the blood adhesion strength of a clot of blood or blood components on a surface is increased compared with an untreated surface.

The device for coagulation diagnosis has, among others, the advantage over other devices that coagulation properties of blood or blood components can also be measured reliably in case of abnormal blood properties which is of high value in such a device.

BRIEF SUMMARY OF THE INVENTION

The present invention pertains to a method of treating the surface of a device which is to be coupled to a clot of blood or to a clot of blood components.

The method may comprise the step of applying a physical, chemical or electrochemical surface treatment such that the surface adhesion strength of coagulated blood or coagulated blood components on the surface is increased compared with the untreated surface.

The method may also comprise applying a physical, chemical or electrochemical surface treatment such that the surface adhesion strength of coagulated blood or coagulated blood components on the surface is increased compared with the untreated surface.

The treatment to the surface may comprise exposing said surface to ionized atoms or molecules such that the surface adhesion strength of coagulated blood or coagulated blood components on the surface is increased compared with the untreated surface.

The ionized atoms or molecules may be generated by a high frequency electrical discharge or static electrical discharge. Electrical discharges with a frequency between (about) 1 kHz and (about) 100 GHz may be applied, more preferably between (about) 10 kHz and (about) 10 GHz.

The ionized atoms and molecules may be generated by an UV laser.

Ar, $O_2$, $N_2$, $H_2O$, air, a rare gas or any mixture thereof may be used as process gas during the exposure of the surface to ionized atoms or molecules.

The surface may be exposed to ionized atoms or molecules for (about) 15 to (about) 500 minutes.

Exposing the surface to ionized atoms may be carried out at a process pressure in the range of (about) 0.1 to (about) 5 mbar.

Exposing the surface to ionized atoms may also be carried out at room temperature.

The surface treatment may be such that the surface texture of the device is modified.

The surface treatment may be such that the modified surface texture has an average peak to peak distance in a range of (about) 25 to (about) 500 nm, preferably in a range of (about) 50 to (about) 250 nm.

The surface treatment may be such that impurities on said surface are eliminated.

The device may be a cup used for analyzing coagulation properties of blood or blood components or a part of such cup.

The device may also be a probe used for analyzing coagulation properties of blood or blood components or a part of such probe.

The device may be made of a biomaterial and may be used for/in (1) implantation into the body of a human or animal or (2) vascular surgery or other vascular treatment.

The device may be made of plastic material or polymer which does not affect the coagulation activity of blood or blood components.

The present invention also pertains to a device which is to be coupled to coagulated blood or to coagulated blood components. The surface properties of at least a part of the surface of the device may be modified by exposure to ionized atoms or molecules to enhance the adhesion strength of coagulated blood or coagulated blood components to the surface.

In such a device, the average peak to peak distance of the surface roughness generated by the exposure to ionized atoms or molecules may be between (about) 25 and (about) 500 nm, more preferably between (about) 50 and (about) 250 nm.

In such a device, the surface average roughness Ra may be below (about) 100 nm, more preferably below (about) 80 nm.

The device may be a cup or a probe used for hemostasis analysis or a part of such cup or such probe.

The device may be a biomaterial used for/in (1) implantation into the body of a human or an animal or (2) vascular surgery or other vascular treatment.

The device may be made of a plastic material or polymer.

The plastic material or polymer does, in a preferred embodiment, not affect the coagulation activity of blood or blood components.

The present invention is also directed to a device for hemostasis analysis including a cup and/or a probe and/or a part of a cup and/or a part of a probe as described above.

The present invention is also directed to a device which is to be coupled to coagulated blood or to coagulated blood components, wherein the surface roughness average Ra is between (about) 5 to (about) 100 nm, more preferably between (about) 5 to (about) 80 nm.

DETAILED DESCRIPTION OF VARIOUS AND PREFERRED EMBODIMENTS

Figure 1:
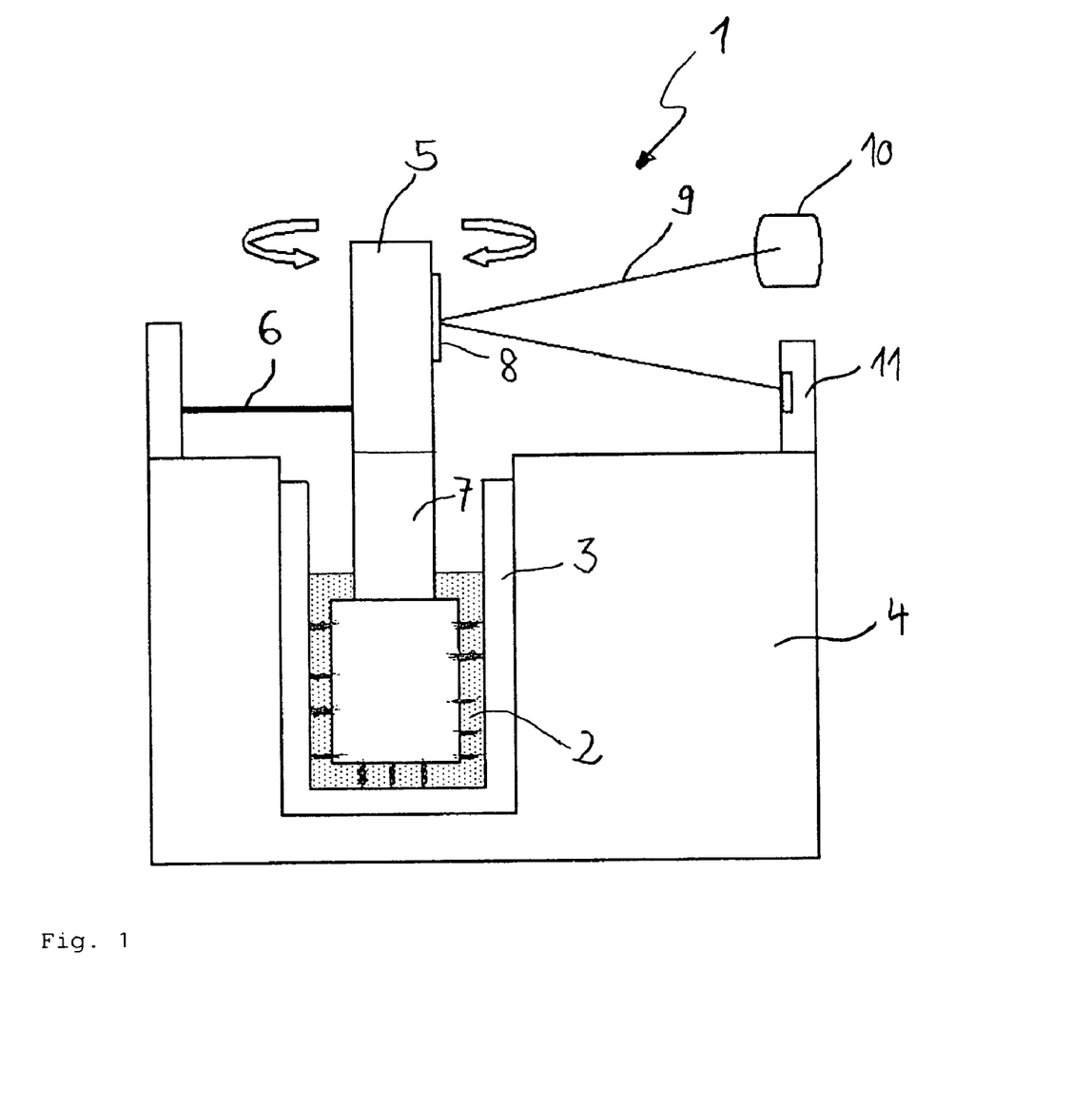
FIG. 1 is a schematic drawing of a device for coagulation diagnosis according to a first embodiment of the invention.

In the following the invention is explained considering a first embodiment of the invention. According to a first embodiment of the invention there is provided a device 1 for measuring coagulating properties of a blood sample 2.

The device 1 includes a cup 3 which is basically cylindrical in shape. The cup 3 is attached to a base 4 such that it is stationary and can not move relative to the base 4.

A shaft 5 is connected to the base 4 for example by a ball bearing such that it is rotatable relative to the cup. A elastic element (fine metal spring) 6 provides a restoring force for the rotational movement of the shaft relative to the cup and base. Detachably connected to the shaft is a probe 7 which has basically a cylindrical outer shape. During the measurement the probe is placed in the inside of the cup such that the blood sample 2 is between the probe and the inner sidewall of the cup.

A mirror 8 is attached to the sidewall of the shaft to reflect a light beam 9 from a light source 10 towards a photo detector 11 so that the rotational position of the shaft 5 can be detected with high precision.

The use of a ball bearing eliminates the high susceptibility to shocks and vibration and other problems of coagulation diagnosis tools wherein the pin is suspended into the cup 3.

In operation the cup is stationary and the probe 7 is rotated back and forth by the elastic element in a range of about ±5°. When the sample in the cup 3 starts to clot, it attaches to the surfaces of the probe 7 and the cup. Thereby the blood clot forms a coupling between the cup 3 and the probe 7 or the shaft 5 which is connected to the probe 7. If a coupling forms between the probe 7 and the cup 3 by means of blood clotting, a torque acts against the rotational movement of the shaft 5 so that the shaft 5 is no longer completely rotated.

The cup 2 and the probe 7 are basically cylindrical in shape wherein the outer diameter of the probe 7 is smaller than the inner diameter of the cup 3 such that the probe 7 can be placed inside of the cup 3.

The cup 2 and probe 7 according to the invention are made of a polymer, preferably Cyrolite®. Cyrolite® has the advantage that it does not affect coagulation activation neither before nor after plasma treatment, because an affected coagulation activation as for example disclosed in U.S. Pat. No. 5,334,611 would lead to a falsification of the measurement results.

According to the invention the method described below was used in the steps of manufacturing the cup 3 and the probe 7.

Figure 2:
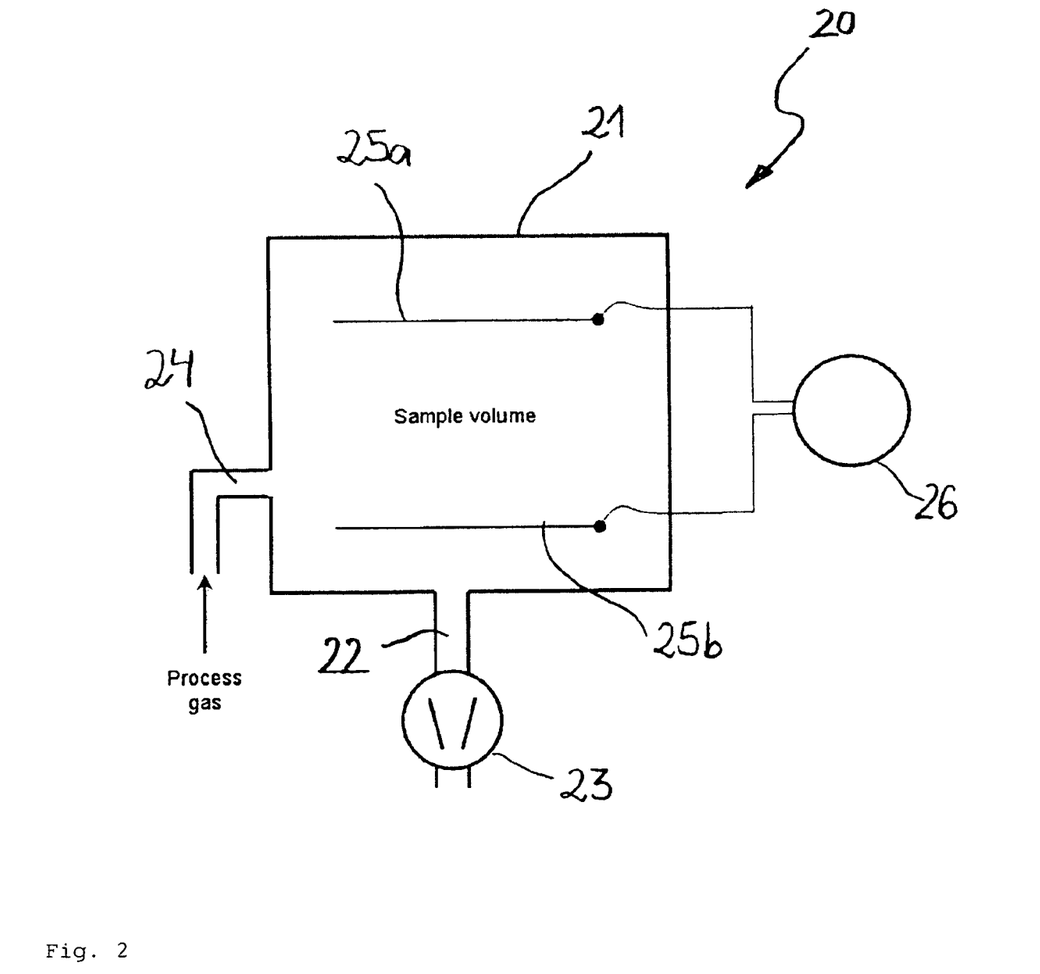
FIG. 2 is a schematic arrangement of a high-frequency plasma device usable for carrying out the method according the second embodiment of the invention.

The surface of the cup 3 and the probe 7 is treated in a plasma chamber system 20 as shown in FIG. 2. The plasma chamber system comprises a receptacle 21 having an outlet 22 connected to a vacuum pump 23 via a not shown valve and having an inlet 24 connected to a not shown process gas supply. In the recipient are provided two electrodes 25a and 25b which are connected to a HF (high frequency) generator 26. In between the two electrodes is the sample volume where the cup 3 and probe 7 are placed to be treated by the plasma generated by the HF generator 26 in between the two electrodes 25a, 25b.

In a particular example the plasma surface treatment was carried out with the following parameters:

Temperature T=293 K (room temperature)

pressure p=1 mbar process time t=60 minutes power density per volume of the probe P/V=10 W/l frequency of the HF generator f=40 kHZ process gas: oxygen The plasma chamber system used for the low pressure plasma surface treatment is a commercial Tetra-100 system from Diener electronic, Nagold, Germany.

Cup 3 and probe 7 are loaded through a not shown load lock into the above mentioned receptacle 21 in the sample volume. Then the receptacle 21 is evacuated to pressures below 1 mbar. After evacuation, oxygen is introduced into the receptacle 21 as a process gas. The pressure in the receptacle 21 is then controlled to a constant value p=1 mbar and an electrical discharge with a frequency f=40 kHz is ignited. The plasma treatment is continued for a time t=60 minutes. After that the cup 3 or probe 7 is removed from the receptacle 21 through the not shown load lock.

Figure 3A:
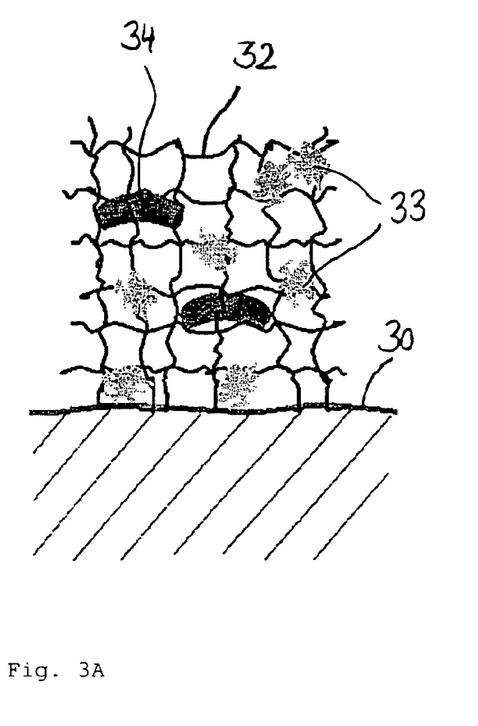
FIG. 3A is a schematic drawing of fibrin and thrombocyte anchoring on a polymer surface before surface plasma treatment.
Figure 3B:
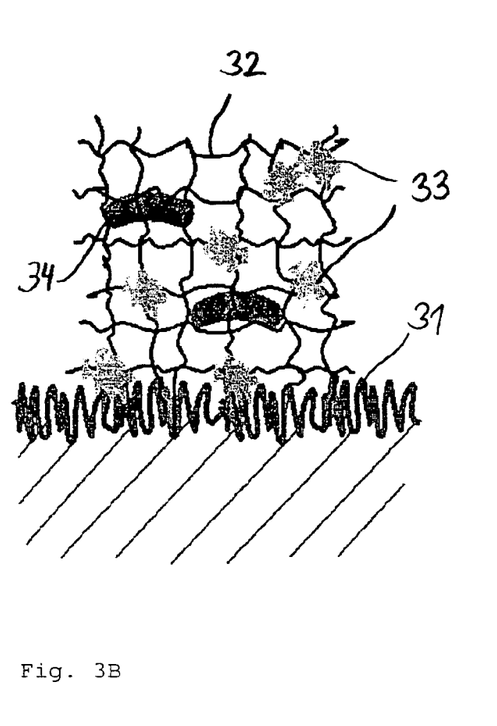
FIG. 3B is a schematic drawing of fibrin and thrombocyte anchoring on a polymer surface after surface plasma treatment.

A first effect of the above described surface treatment according to the invention is that the surface texture of the cup 3 and the probe 7 is such that on a microscopic range the roughness can be characterized by an average peak-to-peak distance of 50 to 250 nm (nanoroughness) as measured between neighbored local maxima on electron microscopy images after the surface treatment (compare FIGS. 4E and 4F) correspond roughly to a roughness average Ra=10-50 nm, where Ra is defined according to the ASME standard B46.1-2002. The roughness of the surface before the described surface treatment is superposed by the before mentioned nanoroughness. An average peak to peak distance of 50 to 250 nm corresponds roughly to a roughness average Ra=10 to 50 nm (measured according to the ASME standard B46.1-2002). FIG. 3A is a schematic drawing of the adhesion of coagulated blood on an untreated surface 30, whereas FIG. 3B is a schematic drawing of the adhesion of coagulated blood on a plasma treated surface 31. There are shown fibrin strands 32, activated thrombocytes 33, and erythrocytes 34 of coagulated blood in FIG. 3A or 3B, respectively. Due to the fact that the peak to peak distance of the surface roughness is in the range of the dimension of the fibrin strands (length of the fibrin strands is about 50 nm), the surface texture obtained by the surface plasma treatment provides ideal conditions for the adhesion of fibrin strands and activated thrombocytes.

Figure 4:
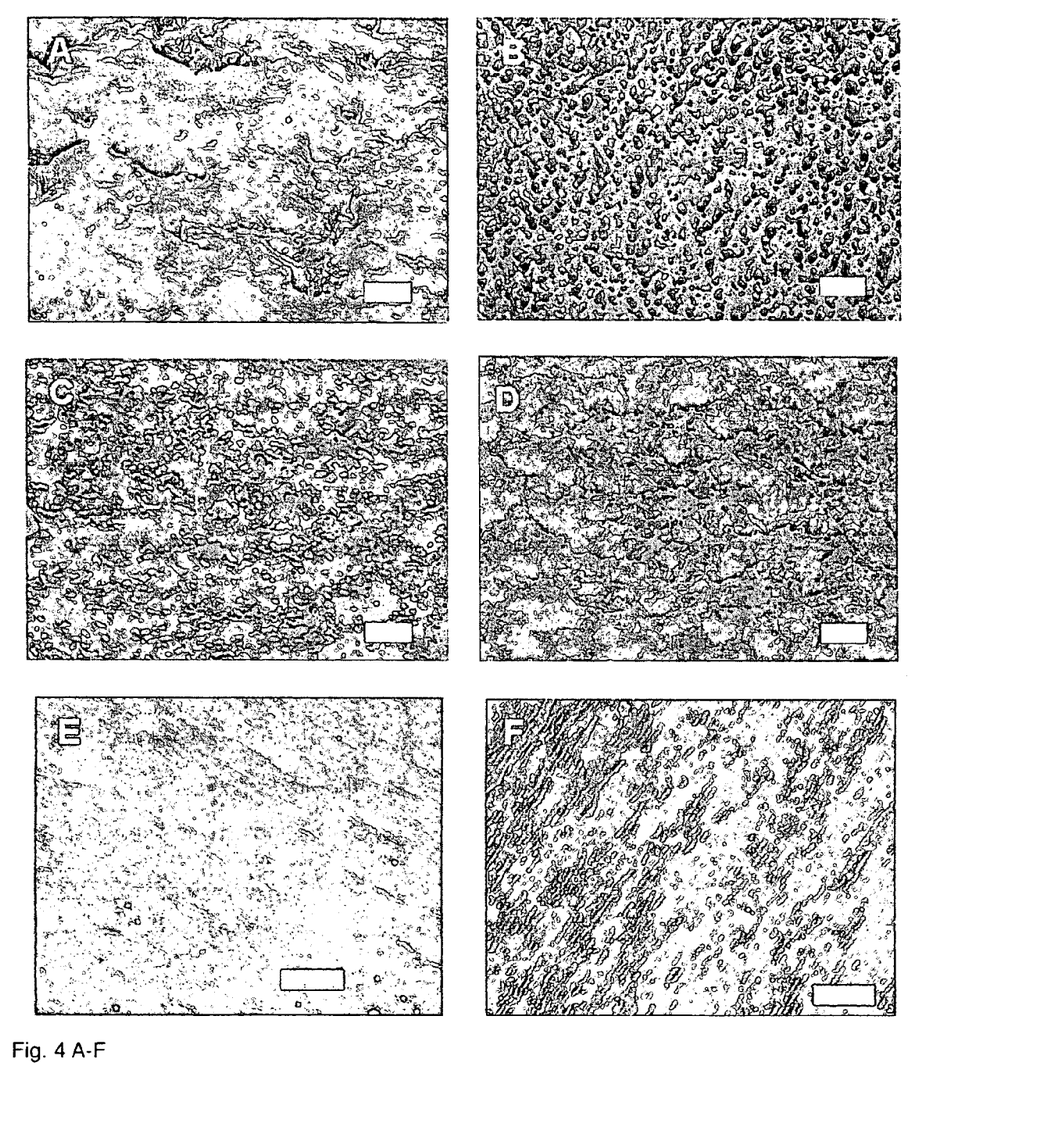
FIG. 4A to 4F show the surface texture of different plasma-treated and untreated polymeric surfaces (A: PTFE before plasma treatment; B: PTFE after plasma treatment, C: POM before plasma treatment; D: POM after plasma treatment; E: Cyrolite® before plasma treatment; F: Cyrolite® after plasma treatment)

In FIGS. 4A to 4F the effect of the plasma treatment on different polymer materials is shown. The white bar in the FIGS. 4A to 4F corresponds to 3 µm. FIG. 4A shows the surface texture of PTFE before the plasma treatment and FIG. 4B the same after the plasma treatment. FIG. 4C shows the surface texture of POM before the plasma treatment and FIG. 4D the same after the plasma treatment. FIG. 4E shows the surface texture of Cyrolite® before the plasma treatment and FIG. 4F the same after the plasma treatment. It can be seen from FIGS. 4B, 4D and 4F that the detailed surface texture after the plasma treatment according to the invention can show rather different shapes in dependence on the polymer material used.

The detailed surface texture after plasma treatment according to the invention can differ also very much in dependence on the used process gas.

A second effect of the above described plasma treatment according to the invention is a strong cleaning effect. Contaminations of the surface are either etched away by pure mechanical interaction with the atoms or molecules in the plasma or even "burned" by chemical reactions with radicals. Surface cleaning is generally of high importance for the quality management of plastic parts used in medical applications: Due to a rather perfect surface purity after plasma treatments independent from the preceding production step(s), any further cost-intensive purification procedures can be omitted. The distribution ratio between etching and burning of contaminations mainly depends on the used process gas, but has only minor influence on the surface properties.

A third effect of the plasma surface treatment according to the invention is the generation of cover layers of incorporated gas molecules or ions. The existence of additional surface charges at the surface provides an increased number of anchoring points for activated fibrin strands or thrombocytes. However, for hemostasis analysis devices the plasma molecules must be carefully selected with respect to the used polymer material to prevent accelerated coagulation activation, since this behavior would falsify the obtained results.

Figure 5:
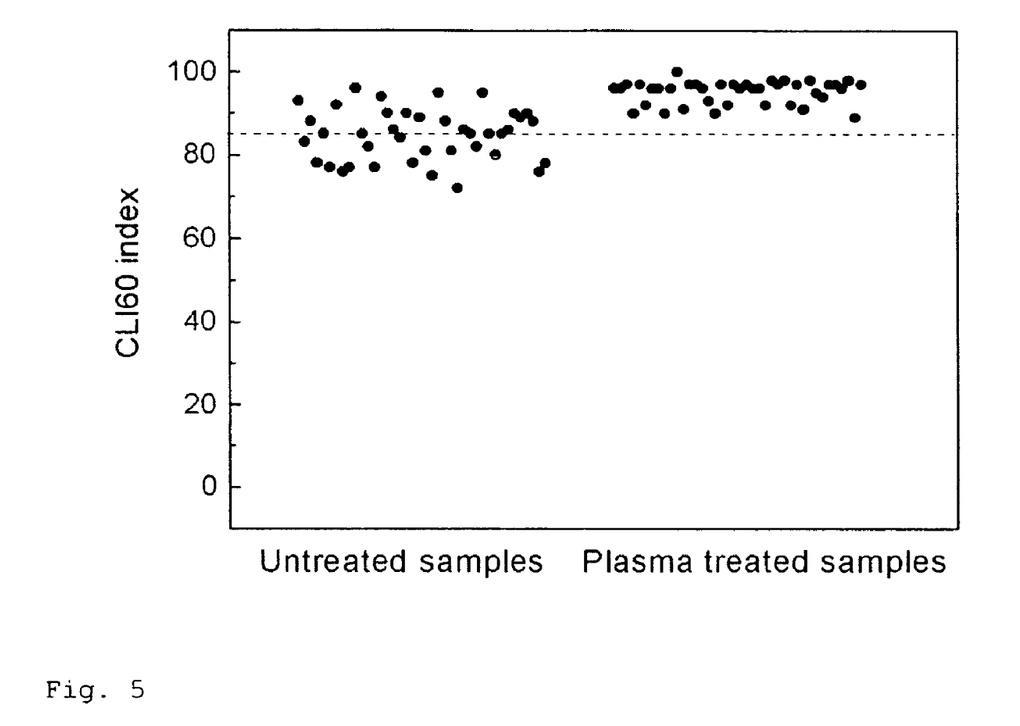
FIG. 5: is a graph showing the CLI60 index of plasma treated cups and probes (right) in comparison to untreated parts (left)

A fourth effect of the above described surface treatment according to the first embodiment of the invention is shown in FIG. 5.

FIG. 5 shows the ratio of the clot firmness measured after 60 minutes to the maximum clot firmness for normal (i.e. non-hyperfibrinolytic) donor blood samples. This ratio, also called CLI60 index, is lowered by partial ruptures of the fibrin network from the surface of the cup or the probe during measurements. Therefore, the CLI60 index is a good indicator for the adhesion strength of coagulated blood on the surface of the cup and the probe.

In total, 20 different donor samples have been measured in duplicate after the addition of thrombocytes (platelets) to a final concentration of about 800.000/µl in a device for coagulation diagnosis as described above. A first set of measurements was carried out using untreated cup and probe. A second set of measurements was carried out using treated cup and probe. The lower values of the CLI60 index for measurements using untreated cup and probe indicate partial ruptures of fibrin strands from the surface of cup and probe. The measured CLI60 index using treated cup and probe for the same blood samples are higher and therefore indicate a better adhesion of the coagulated blood to the surface of the cup and the probe.

Values below 85% (dashed line in FIG. 5) are commonly indicative for hyperfibronolitic malfunctions of the hemostasis balance. Therefore, it is important to measure values above 85% for normal blood samples without any malfunction. Only in that case a hyperfibronolitic malfunction can be determined reliably by coagulation diagnosis. The value of the CLI60 index was above 85% for all measurements using treated cup and probe, whereas for the measurements using untreated cup and probe many measurements gave values below 85%.

Since the CLI60 index (or the CLI45 index obtained after 45 min) is often used for the diagnosis of hyperfibrinolysis, lower values due to insufficient surface adhesion of the fibrin network are a potential risk in hemostasis analysis. Since the blood of patients with considerably increased platelet content tends to tear off the surface due to a denser clot packing, mistakable measurements cannot be excluded. This danger could now be satisfactorily eliminated by applying plasma treatments for the disposables used in this method.

Figure 6A:
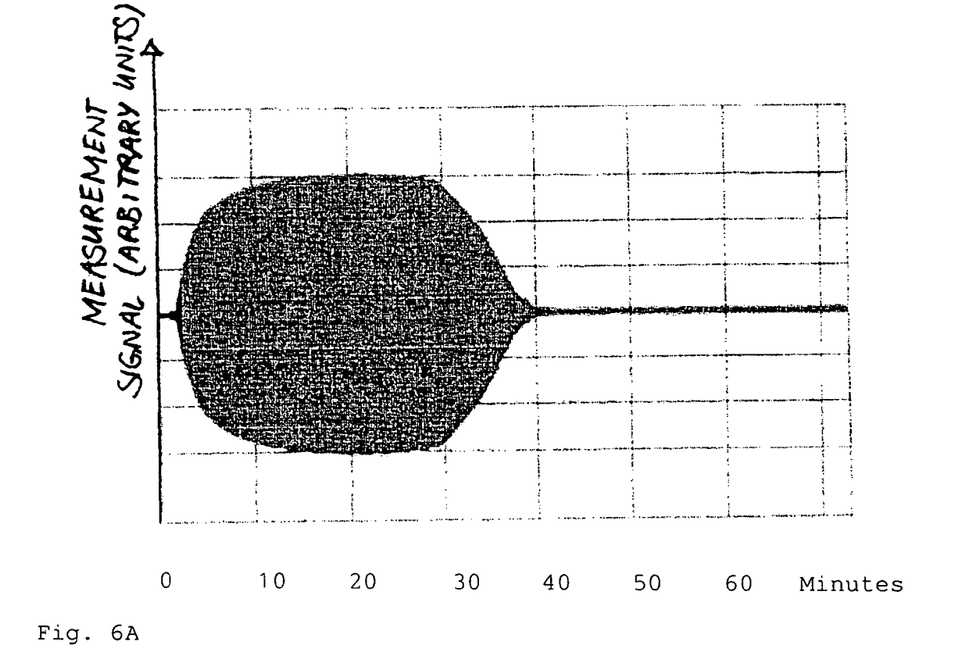
FIGS. 6A and 6B are diagrams showing a thromboelastometric measurement with plasma-treated cup and probe (A) and with untreated cup and probe (B)
Figure 6B:
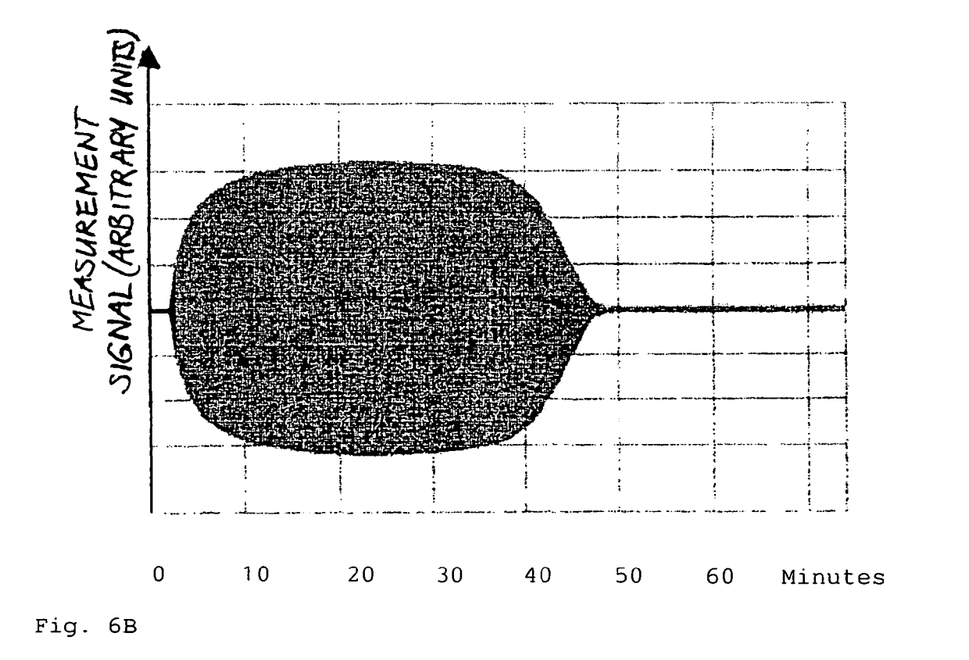

A fifth effect of the plasma treatment described above is revealed for samples in which hyperfibrinolysis is artificially induced by adding urokinase. Identical blood samples were treated with urokinase to simulate hyperfibrinolytic behavior. The result of a measurement using cup and probe with a treated surface is shown in FIG. 6A, whereas the result of a measurement using cup and probe with untreated surface is shown in FIG. 6B. In the case of using cup and probe according to the first embodiment, the pathological pattern of hyperfibrinolysis is accelerated by about 10 to 15 min compared to the measurement using cup and probe without any surface treatment and enables in this way faster medical action, e.g. in critical surgery situations.

Accordingly, the method disclosed here is highly capable to improve the coagulation analysis in a multiple manner.

Figure 7:
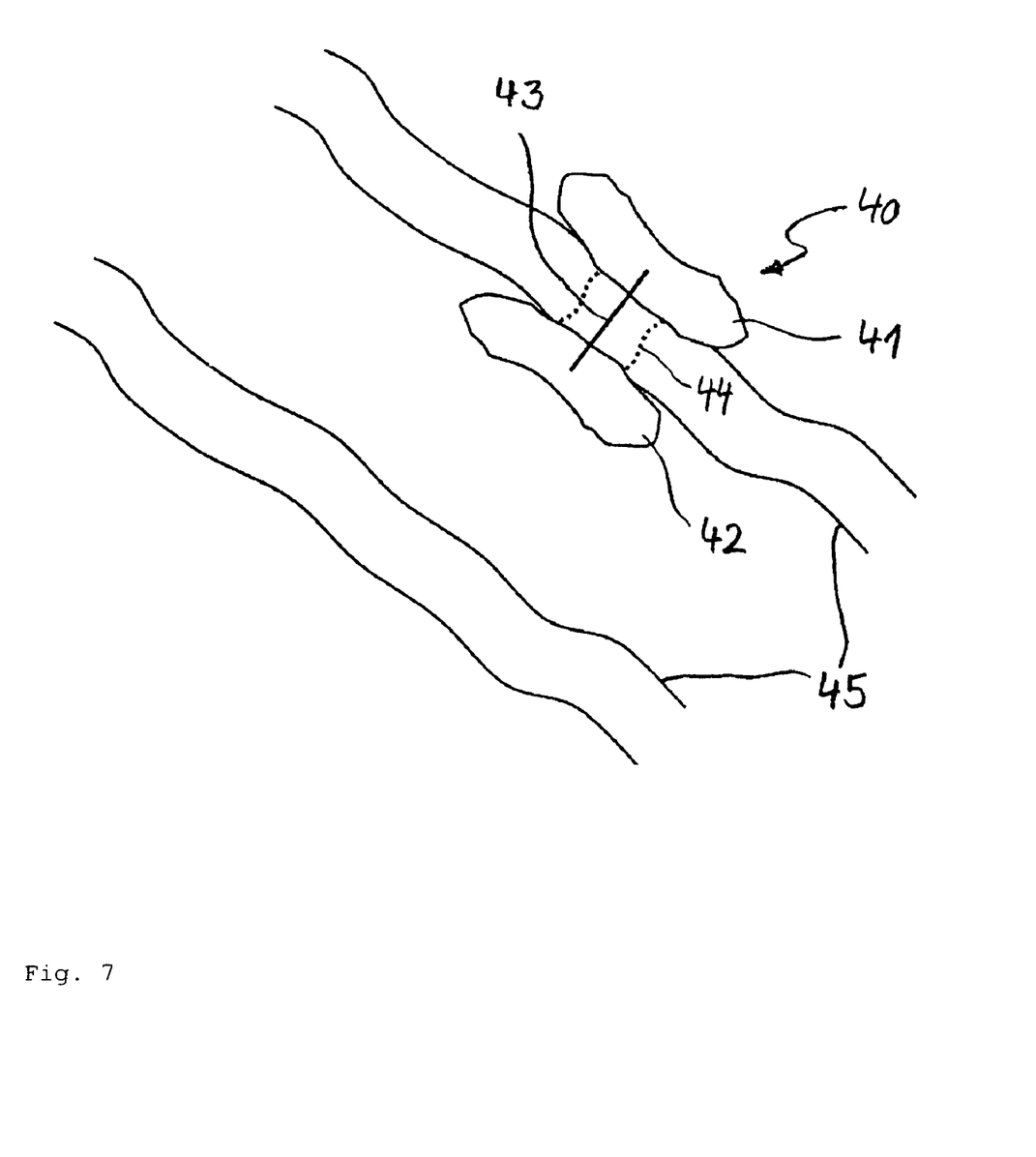
FIG. 7 is a schematic drawing of an artery sealing according to the second embodiment of the invention.

An artery sealing according to a second embodiment of the invention can be seen in FIG. 7. The artery sealing 40 comprises an outer sealant 41 and an inner sealant 42. The outer sealant 41 and the inner sealant 42 are connected by a connection piece 43 and sandwich an arteriotomy (artery puncture or injury) 44 to create hemostasis of a punctured artery 45.

The inner sealant 42 is placed within the artery 45 whereas the outer sealant 41 is placed opposite to the inner sealant 42 outside of the artery 45. The inner and outer sealant 42, 41 are preferably made of a bio-absorbable polymer (e.g. collagen, polyestheramide, polyglycolic acid, polylactic acid, polydioxanone) and treated by the above described surface plasma treatment to obtain a good sealing effect. The plasma treatment reduces considerably the probability of blood clot ruptures from the sealing which can cause embolism or apoplexy.

In the second embodiment, the same effects are obtained by the plasma treatment according to the invention as in the above described first embodiment.

Although most polymeric surfaces show in general a good ability to bind blood-inherent coagulation components like thrombocytes and fibrin, the maximum tearing force is not adequate in the case of higher blood pressures or vascular motions. In view of this, improvements of the blood anchoring ability at artificial surfaces enable the use of highly sufficient vascular sealings.

Cup and probe according to the first embodiment of the description are described to be preferably made from Cyrolite®. However, it could be also made from any other polymer which does not affect coagulation activation even after plasma treatment. Further non-limiting examples for such polymers are polyethylene or acrylic plastic (e.g. polymethyl methacrylate). It was described to generate a nanoroughness with an average peak to peak distance between 50 and 250 nm. However, any nanoroughness with an average peak to peak distance below 500 nm could be used to increase the adhesion strength of coagulated blood or coagulated blood components and can be produced by the above mentioned method in dependence of the employed discharge intensity and treatment time. An average peak to peak distance below 500 nm corresponds roughly to a roughness average Ra below 100 nm (measured according to the ASME standard B46.1-2002).

The cup and probe are described to be basically cylindrical in shape and having basically a cylindrical outer shape, respectively. However, as the person skilled in the art will appreciate other shapes of the cup and/or probe are within the scope of the present invention. In particular, in certain embodiments, any shape of the cup and probe that allows (1) the probe to be placed inside of the cup and (2) the inner side wall of the cup to act as a functional surface of the device which is to be coupled to coagulated blood or to coagulated blood components is within the scope of the present invention. In particular, any cup/probe shape combination that allows blood placed between the inner sidewall of the cup and the probe to form, upon clotting, a coupling between cup and the probe as described elsewhere herein is within the scope of the present invention.

The artery sealing according to the second embodiment was described as an example for a biomaterial being treated with the plasma treatment according to the invention. However, the plasma treatment can be used for any other biomaterial for medical applications wherein the surface properties of the biomaterial must allow a sufficient adhesion of coagulated or coagulating blood. In the case of implants the blood clot serves as a scaffold for tissue regeneration.

The surface plasma treatment according to the above-described particular example of the invention was described using oxygen as a process gas. However, several other process gases could be used and further non-limiting examples are: nitrogen ($N_2$), rare gases (e.g. Ar), air, $H_2O$, a $CF_4/O_2$-mixture or any mixtures thereof.

The surface plasma treatment according to the above described particular example of the invention was described to be carried out at low pressure (1 mbar). However, it is also possible to apply plasma treatment in any other pressure regime. Preferably the process pressure is in a range between 0.5 mbar and 5 bar.

The surface plasma treatment according to the above described particular example of the invention was described to be applied for a process time of 60 min. However, other process times are possible. The above described effects of the plasma treatment are more intense as the process time is increased. Longer process times result in higher manufacturing costs. Preferably the process time is in a range between 15 minutes and 12 hours.

Other power densities of the plasma are possible. The higher the power density of the plasma the shorter times are needed to obtain the desired effects described above. However, too high power densities will result in melting or destroying the treated parts. Preferably, the power density is in a range between 1 W/l and 100 W/l.

The surface plasma treatment according to the invention is not limited to using a HF plasma having a frequency of 40 kHz. Using a plasma with any other frequency is possible (e.g. radio frequency 13.56 MHz or microwave frequency 2.45 GHz or even a static electrical field). Preferably, the plasma frequency is in a range between 1 kHz and 10 GHz.

The surface plasma treatment according to the invention is not limited to plasma treatment carried out at 293 K. Other temperatures can be used. Higher temperatures will lead to a better outgassing of the parts to treat while lower temperatures reduce the arising gas amount. Preferably, the process temperature is in a range between 200 K and 360 K.

It is described above to change the chemical activity, textural structure and aseptic purity of a polymeric surface by plasma treatment. However, it is also possible to change the chemical activity, textural structure and aseptic purity of a polymeric surface by the treatment of the surface with an UV laser activated process gas instead of a plasma activated process gas.

It was described to modify a surface by incorporating additional charges, atoms, molecules, ions or functional groups into the surface to provide an increased number of anchoring points for activated fibrin strands or thrombocytes. However, it is also possible to incorporate functional spots enhancing the adhesion of coagulated blood into the surface by chemical methods instead of by treatment by ionized atoms or molecules.

According to the above-described method of surface plasma treatment, one part is exposed to the plasma in the plasma chamber system at a time. However, it is also possible to treat more than one single part at a time, for example by employing one or several trays or a continuously rotating drum in the plasma chamber system.

As the person skilled in the art will appreciate, other modifications of the above described embodiments are also within the scope of the present invention.

What is claimed is:

1. A method for treating a surface of a device which is to be coupled to a clot of blood or to a clot of blood components, the method comprising
applying a physical, chemical or electrochemical surface treatment to said surface so that a surface adhesion strength of coagulated blood or coagulated blood components on said surface is increased compared to a surface adhesion strength of coagulated blood or coagulated blood components on said surface prior to applying said physical, chemical or electrochemical surface treatment, wherein the surface treatment comprises exposing said surface to ionized atoms or molecules and provides a CLI60 index (clot lysis index at 60 minutes) of above 85% for donor blood samples showing no hyperfibrinolysis.

2. The method of claim 1, wherein said ionized atoms or molecules are generated by high frequency electrical discharge(s) or static electrical discharge(s).

3. The method of claim 2, wherein said electrical discharge(s) is/are applied with a frequency of between about 1 kHz and about 100 GHz.

4. The method of claim 3, wherein said electrical discharge(s) is/are applied with frequency between about 10 kHz and about 10 GHz.

5. The method of claim 1, wherein the ionized atoms and molecules are generated by an UV laser.

6. The method of claim 1 further comprising providing Ar, $O_2$, $N_2$, $H_2O$, air, a rare gas or any mixture thereof as process gas while exposing said surface to ionized atoms or molecules.

7. The method of claim 1, wherein said surface is exposed to ionized atoms or molecules for about 15 to about 500 minutes.

8. The method of claim 1, wherein said surface is exposed to ionized atoms at process pressures in the range of about 0.1 to about 5 mbar.

9. The method of claim 1, wherein said surface is exposed to ionized atoms at room temperature.

10. The method of claim 1, wherein said surface treatment is a plasma surface treatment that provides additional surface charges at the surface of the device as anchoring points for activated fibrin strands and thrombocytes.

11. The method of claim 10, wherein plasma molecules of said plasma surface treatment are selected so as to prevent accelerated coagulation activation.

12. The method of claim 1, wherein said surface treatment eliminates impurities on said surface.

13. A device which is to be coupled to coagulated blood or to coagulated blood components comprising
a surface having surface properties,
wherein at least a part of said surface is exposed to ionized atoms or molecules so that the surface properties result in surface modifications that enhance the adhesion strength of coagulated blood or coagulated blood components to the surface, wherein the surface modification provides for a CLI60 index (clot lysis index at 60 minutes) of above 85% for a donor blood sample showing no hyperfibrinolysis.

14. The device of claim 13 wherein the device is a cup or a probe for hemostasis analysis or a part of such cup or such probe.

15. A device for hemostasis analysis including a cup and/or a probe and/or a part of a cup and/or a part of a probe according to claim 14.

16. The device of claim 13,
wherein said at least part of said surface is exposed to a surface treatment and the surface treatment essentially consists of exposing said surface to ionized atoms or molecules so that the surface properties of said surface are modified to enhance the adhesion strength of coagulated blood or coagulated blood components to the surface and
wherein the device comprises a biomaterial suitable for implantation into a human or an animal body or a biomaterial suitable for use in vascular surgery or another vascular treatment.

17. The device of claim 13, wherein the device comprises plastic material(s) or polymer(s).

18. The device according to claim 17, wherein the plastic material(s) or polymer(s) do not affect the coagulation activity of blood or blood components.

\* \* \* \* \*